United States Patent
Wang et al.

(10) Patent No.: US 7,805,274 B2
(45) Date of Patent: Sep. 28, 2010

(54) STRUCTURE AND METHODOLOGY FOR CHARACTERIZING DEVICE SELF-HEATING

(75) Inventors: Ping-Chuan Wang, Hopewell Junction, NY (US); Paul A. Hyde, Essex Junction, VT (US); Kevin Kolvenbach, Walden, NY (US); Giuseppe La Rosa, Fishkill, NY (US)

(73) Assignee: International Business Machines Corporation, Armonk, NY (US)

( * ) Notice: Subject to any disclaimer, the term of this patent is extended or adjusted under 35 U.S.C. 154(b) by 757 days.

(21) Appl. No.: 11/559,120

(22) Filed: Nov. 13, 2006

(65) Prior Publication Data

US 2008/0112458 A1    May 15, 2008

(51) Int. Cl.
*G01N 25/20* (2006.01)

(52) U.S. Cl. .................. 702/130; 702/132; 702/136; 257/388; 257/412; 257/413; 438/14; 438/16; 438/17; 438/18; 374/43

(58) Field of Classification Search ............... 702/130, 702/132, 136; 257/388, 412–413; 438/652, 438/14, 16–18; 374/43
See application file for complete search history.

(56) References Cited

U.S. PATENT DOCUMENTS

| 3,569,704 | A | 3/1971 | Mitchell |
| 6,423,604 | B1 | 7/2002 | Long et al. |
| 7,039,888 | B2 | 5/2006 | Steinmann et al. |
| 2006/0024852 | A1* | 2/2006 | Joshi et al. .................. 438/18 |
| 2006/0047474 | A1* | 3/2006 | Hyde et al. ................. 702/182 |

FOREIGN PATENT DOCUMENTS

| DE | 3831012 | 3/1990 |
| DE | 3930006 | 3/1991 |
| WO | 94/10559 | 5/1994 |

\* cited by examiner

*Primary Examiner*—Sujoy K Kundu
(74) *Attorney, Agent, or Firm*—Greenblum & Bernstein P.L.C.; Joseph P. Abate

(57) ABSTRACT

A method comprises determining a poly-gate temperature for a given device and determining channel temperatures of monitor devices. The method further includes extrapolating channel temperatures of the monitor devices to obtain a channel temperature for the given device. The difference in temperature ($\Delta T$ value) is determined for the given device based on the poly-gate temperature and the channel temperature. A device comprises a heating device having a poly gate with at least one contact at each end thereof and a plurality of monitor device spaced at known distances from the heating device

18 Claims, 12 Drawing Sheets

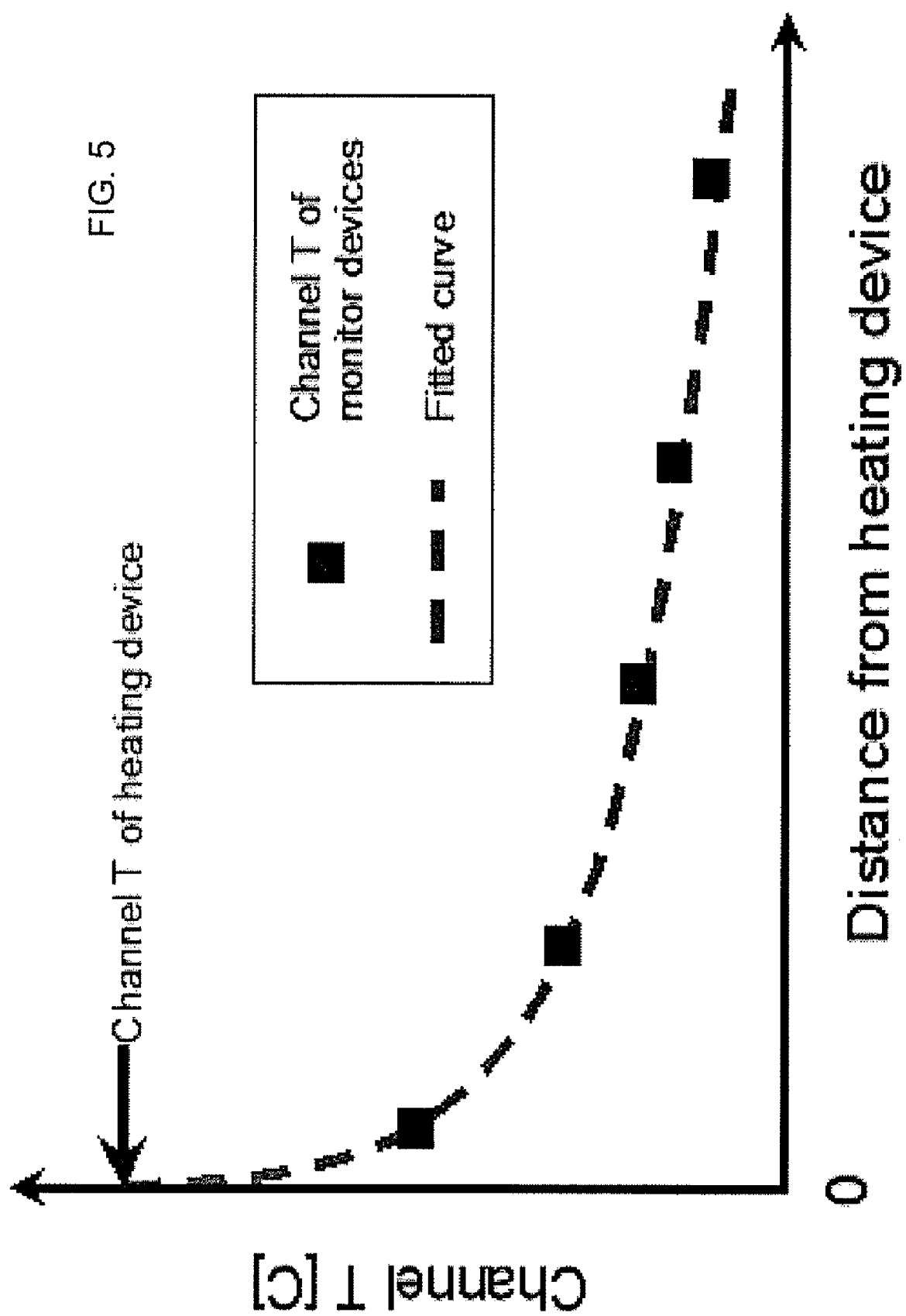

STRUCTURE AND METHODOLOGY FOR CHARACTERIZING DEVICE SELF-HEATING

FIELD OF THE INVENTION

The invention relates to a structure and methodology for characterizing device self-heating and, more particularly, to a structure and method for determining temperatures of devices with different characteristics and under different operating conditions.

BACKGROUND DESCRIPTION

Devices in advanced microelectronics employ silicon-on-insulator (SOI) technology for improved performance, where the active area of a device is in a thin silicon layer, isolated from the bulk silicon substrate by a buried oxide (BOX) layer. The BOX provides electrical isolation from the substrate for improved field distribution in the active area, but it also forms a major barrier for heat to dissipate from devices under severe operating or stress conditions down to the substrate. As a result, the devices of interest are at significantly higher temperature than the ambient or substrate temperature.

More specifically, a device such as a FET is built on a substrate and, as is well known, includes a channel, gate and oxide material. Within the channel to gate junction, self-heating is evident, typically occurring due to source voltage Vs, drain voltage Vd, and gate voltage Vg. For example, as the voltages are applied to the source, gate and drain of the device, internal heating begins to occur, typically which are non-uniform in distribution and degree. During the operational states of the circuits, the self-heating is also known to be non-uniform throughout the topology of the circuit.

Knowing the exact device temperature under a specified condition is critical in characterizing and modeling the device and its reliability. In one methodology, the device temperature is indirectly calculated by temperatures of the monitor devices at various distances from the device of interest. However, it is well known that the device temperature depends on the environment (such as the RX area, STI location, the number of nearby metal contacts/wires, etc) around the device of interest. Therefore, the temperature obtained using this method is only valid for the particular device measured with a given configuration and environment. This estimated temperature, of course, may be quite different from that of a different device of interest.

Also, various models are utilized to estimate the generated heat such as the Berkeley Short-channel IGFET Model for MOS transistors (BSIM). The BSIM model approximates the internal operations of a circuit at a certain design stage. These models use parameters of the circuit components to assist in the design of the final integrated circuit using mathematical statistical models. Although the BSIM is a good method to approximate the internal temperature of the integrated circuit, using approximations and statistical models only produce estimated results which cannot accurately account for the variations in temperature throughout the cross sections of the final integrated circuit product.

Accordingly, there exists a need in the art to overcome the deficiencies and limitations described hereinabove.

SUMMARY OF THE INVENTION

In a first aspect of the invention, a method comprises determining a poly-gate temperature for a given device and determining channel temperatures of monitor devices. The method further includes extrapolating channel temperatures of the monitor devices to obtain a channel temperature for the given device. The difference in temperature ($\Delta T$ value) is determined for the given device based on the poly-gate temperature and the channel temperature.

In another aspect of the invention, the method comprises measuring a poly-gate temperature for a heating device and also determining channel temperatures of monitor devices by use of sub-threshold slopes. The method further includes extrapolating channel temperatures of the monitor devices to a zero distance to the heating device in order to obtain a channel temperature of the heating device. A temperature difference ($\Delta T$ value) is determined for the heating device between the channel temperature and the poly-gate temperature.

In another aspect of the invention, a device comprises a heating device having a poly gate with at least one contact at each end thereof and a plurality of monitor device spaced at known distances from the heating device.

BRIEF DESCRIPTION OF THE DRAWINGS

FIG. 5 shows a graph extrapolating channel temperature to zero distance from a heating device in accordance with the invention;

DETAILED DESCRIPTION OF EMBODIMENTS OF THE INVENTION

The invention relates to a structure and methodology for characterizing device self-heating. The structure and methodology characterizes the $\Delta T$ between a poly-gate and a channel across the gate oxide. The $\Delta T$ value is a thermal property of the gate oxide and, to the first order, does not depend on the configuration and environment of the device. More specifically, $\Delta T$ is the temperature difference between gate temperature and channel temperature of a given device under given conditions.

By implementing the invention, the device channel temperature can be exactly determined once the poly-gate resistance is measured, regardless of its configuration and environment. In embodiments, the methodology for determining the $\Delta T$ value includes measuring the poly-gate temperature of a heating device and "projecting" the channel-temperature of the heating device. The methodology described herein may be used for reliability or design testing purposes.

Figure 1A:
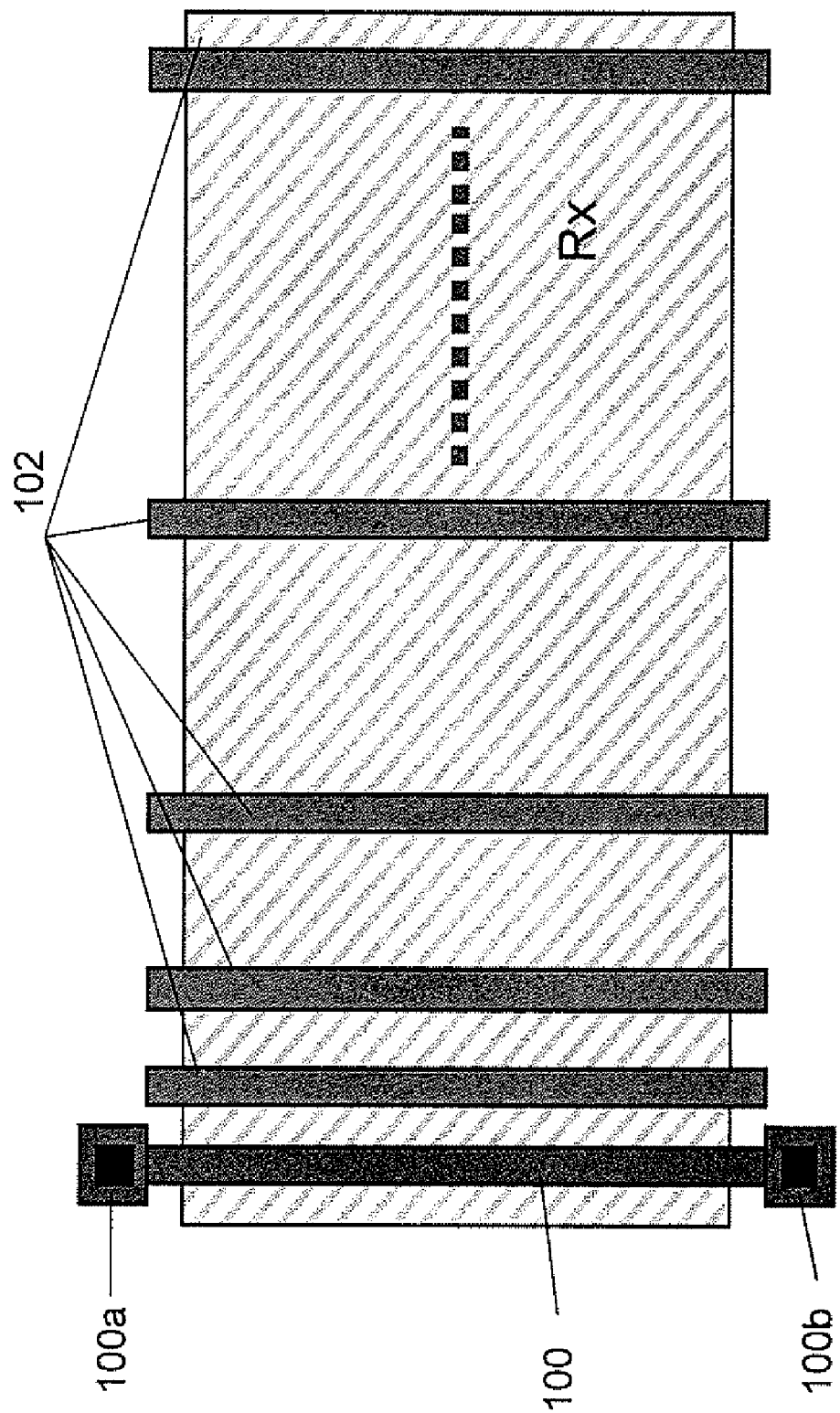
FIGS. 1a and 1b show devices in accordance with aspects of the invention.
Figure 1B:
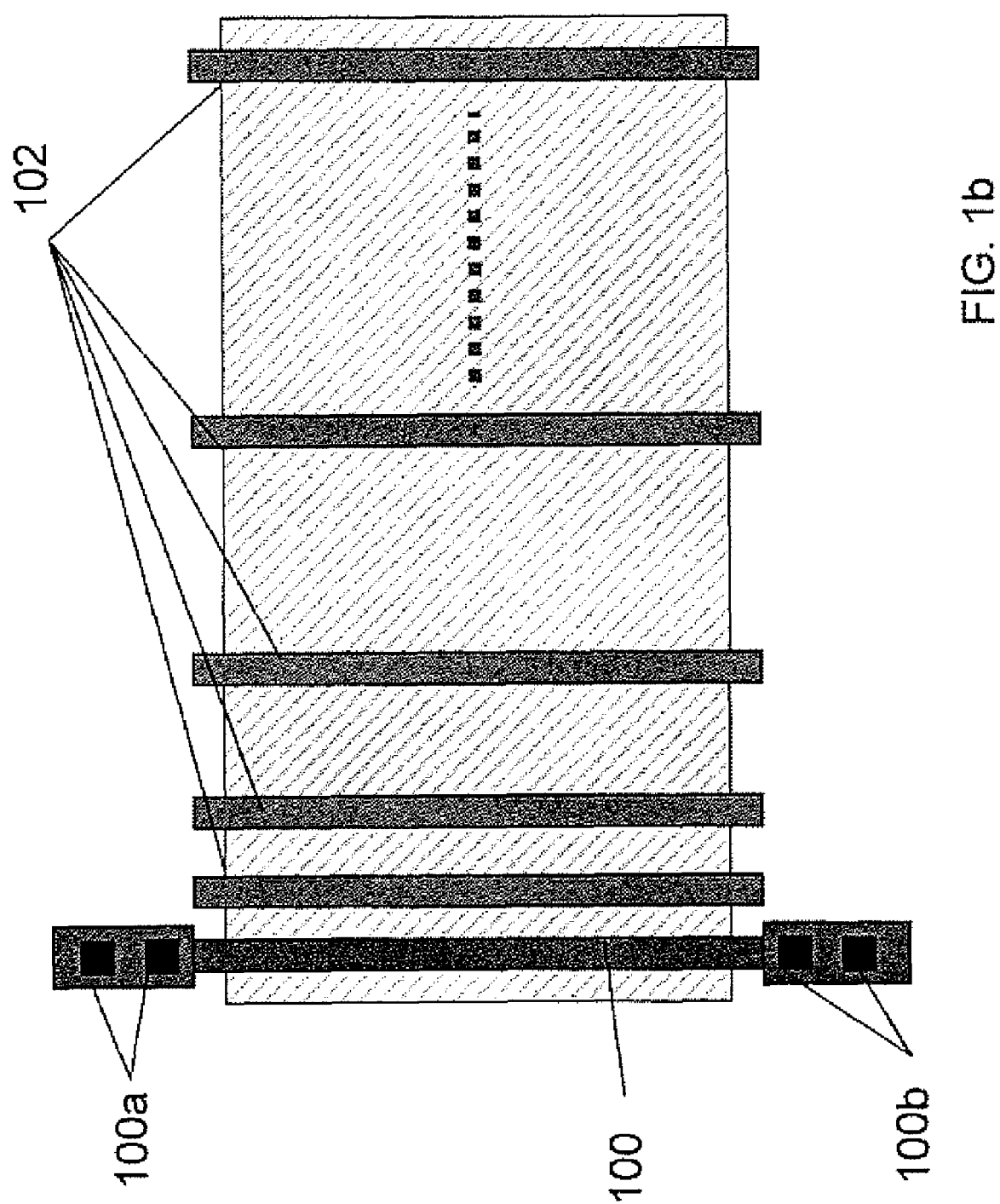

FIG. 1a shows a structure in accordance with the invention. The structure includes a self-heating device 100 and a plurality of monitor devices 102 on an Rx. The poly gate of the self-heating device 100 includes contacts 100a, 100b, at both ends thereof. The contacts 100a, 100b are configured to allow the measurement of poly-gate resistance which, in turn, is used to determine the poly-gate temperature, directly, during device operation. The accuracy in measuring the poly-gate resistance can be improved by using a 4-point probe structure (Kelvin contact), which requires one additional wiring pad at each end of the poly gate as shown in FIG. 1b.

In embodiments, the channel temperature of the monitor devices 102 is determined at various distances by their sub-threshold slopes. By extrapolation, the channel temperature of the heating device 100 can be calculated. In this way, the $\Delta T$ between the poly-gate temperature and the channel temperature can be obtained for the given gate oxide thickness. By knowing the $\Delta T$ value, the device channel temperature over various configurations and operating conditions can be determined once the poly-gate temperature is directly measured with the methodology of the invention.

Figure 2:
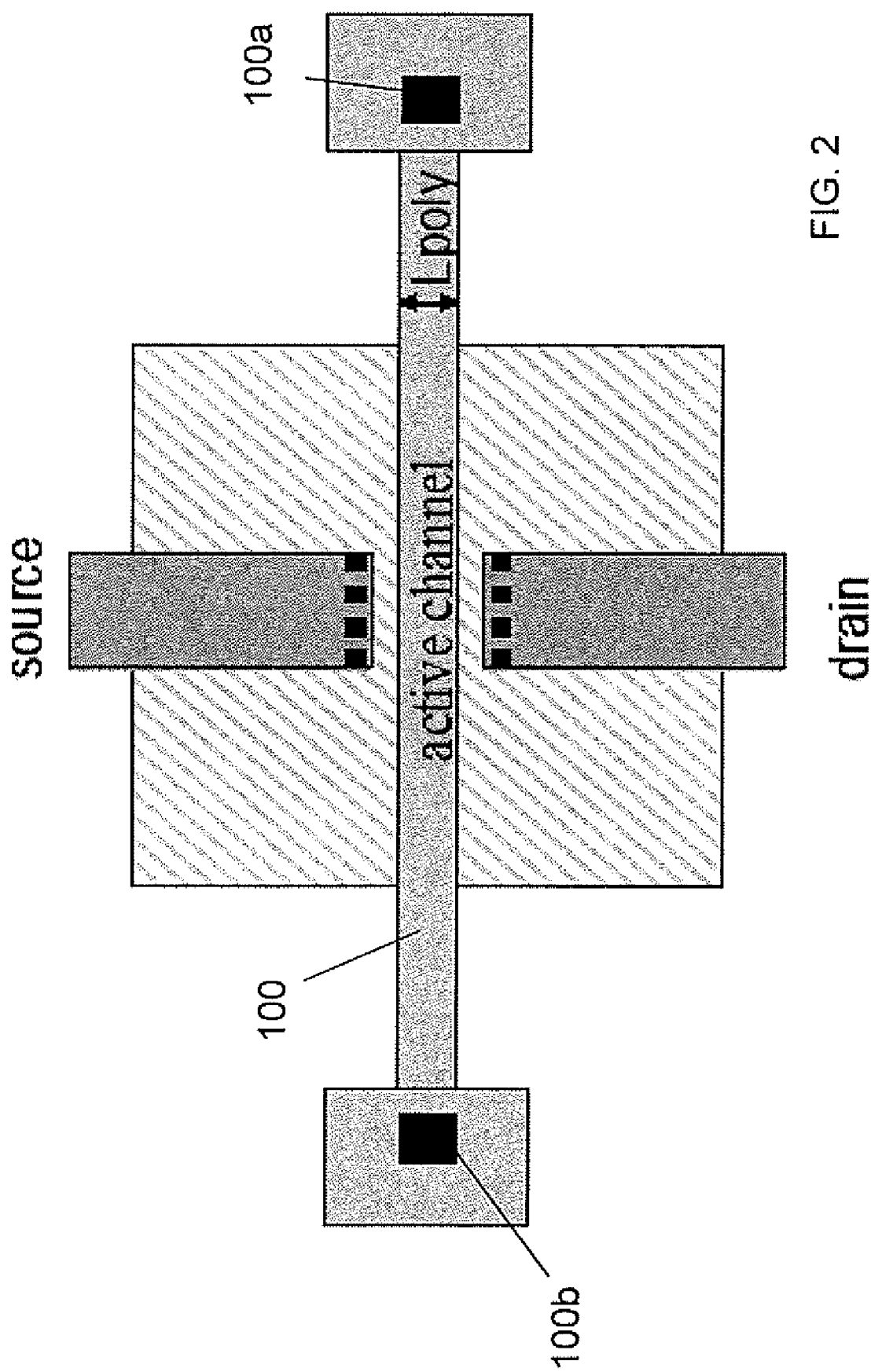
FIG. 2 shows an exploded view of the device of FIG. 1a in accordance with the invention.

FIG. 2 shows a detailed view of the heating device 100 of FIG. 1a. In particular, the heating device includes an active channel, between a source and a drain region. The poly gate includes two contacts 100a, 100b. In the embodiment of FIG. 1b, the poly gate includes four contacts. In either embodiment, the structure is a standard FET with additional gate contact(s). The gate contacts allow the measurement of poly-gate resistance during device operation, as discussed in more detail below.

Figure 3A:
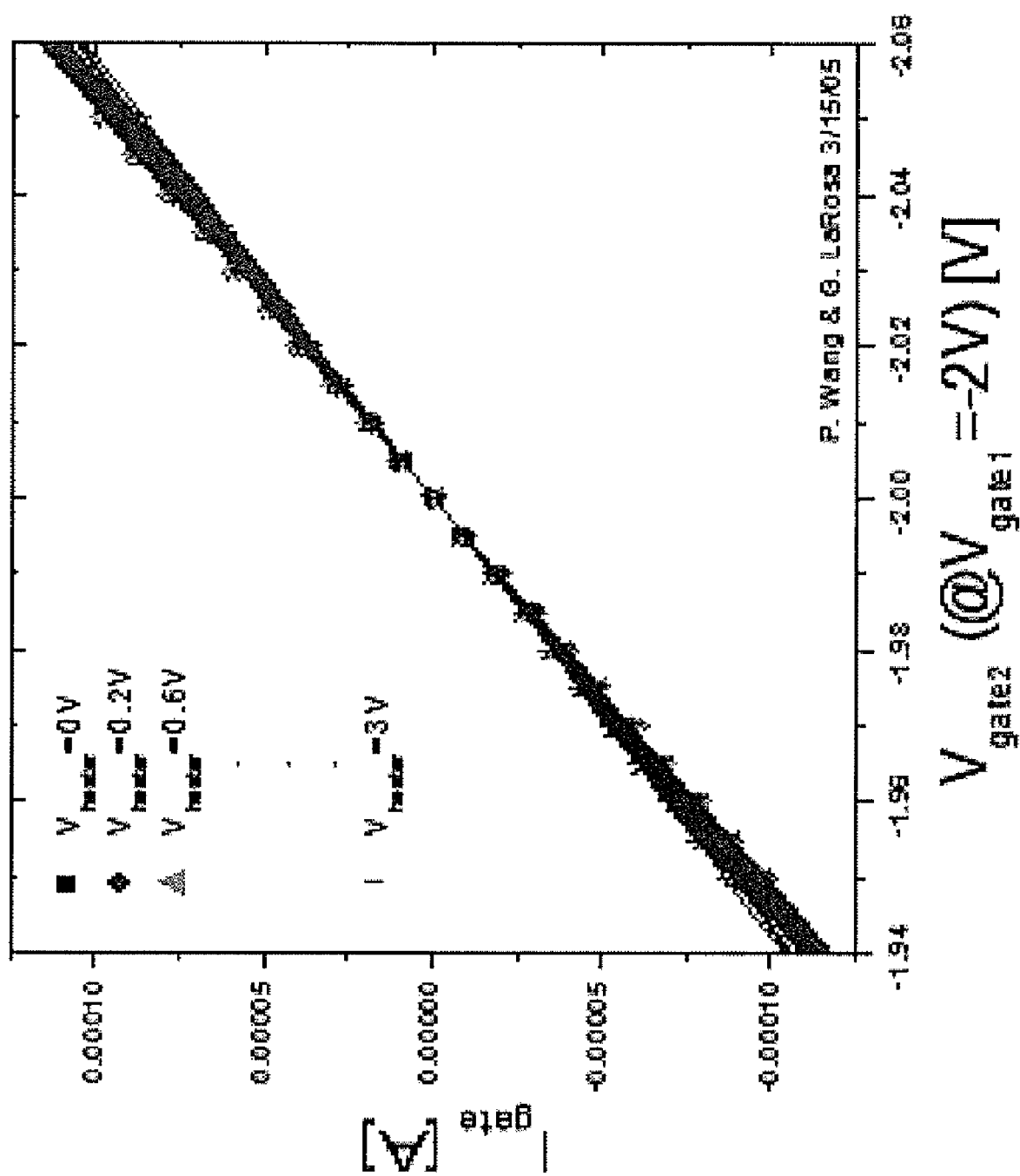
FIG. 3a is a graph showing gate voltage plotted against gate current.

FIG. 3a is a calibration plot of voltage versus current flowing through the gate for a test device at different gate temperatures from the respective heater powers. In this plot, the device is not powered up. In this example, the voltage of the heating device 100 is measured at:

$V_{heater}$=0V (room temperature);
$V_{heater}$=0.2V;
$V_{heater}$=0.6V; and
$V_{heater}$=3V.

As should be understood, temperatures of the heating device 100 are known for each $V_{heater}$. For example, in one non-limiting illustrative example, the temperature of the device at $V_{heater}$=0.2V is approximately 30° C. and the temperature of the device at $V_{heater}$=3V is about 120° C. It should be understood that the voltages shown herein are the voltages applied to the heaters near the device of interest, and are provided for illustrative purposes and should not be construed as a limiting feature to the invention. Thus, it should be understood that other voltage values, as well as other heating methods for calibration such as using a temperature controlled chuck, can be implemented using the principles of the invention.

In this calibration plot, one gate contact is kept at a Vg value (e.g., -2V), while the other gate contact is swept between +/-50 mV around Vg (-1.95V ~2.05V); although other sweep values are also contemplated by the invention. Also, the source and drain voltages are kept grounded during the measurements so that there is minimal current, and thus minimal self heating, in the device. The slopes of the sweeps are indicative of the resistance of the heating device 100. (Resistance is equal to voltage divided by current.)

Figure 3B:
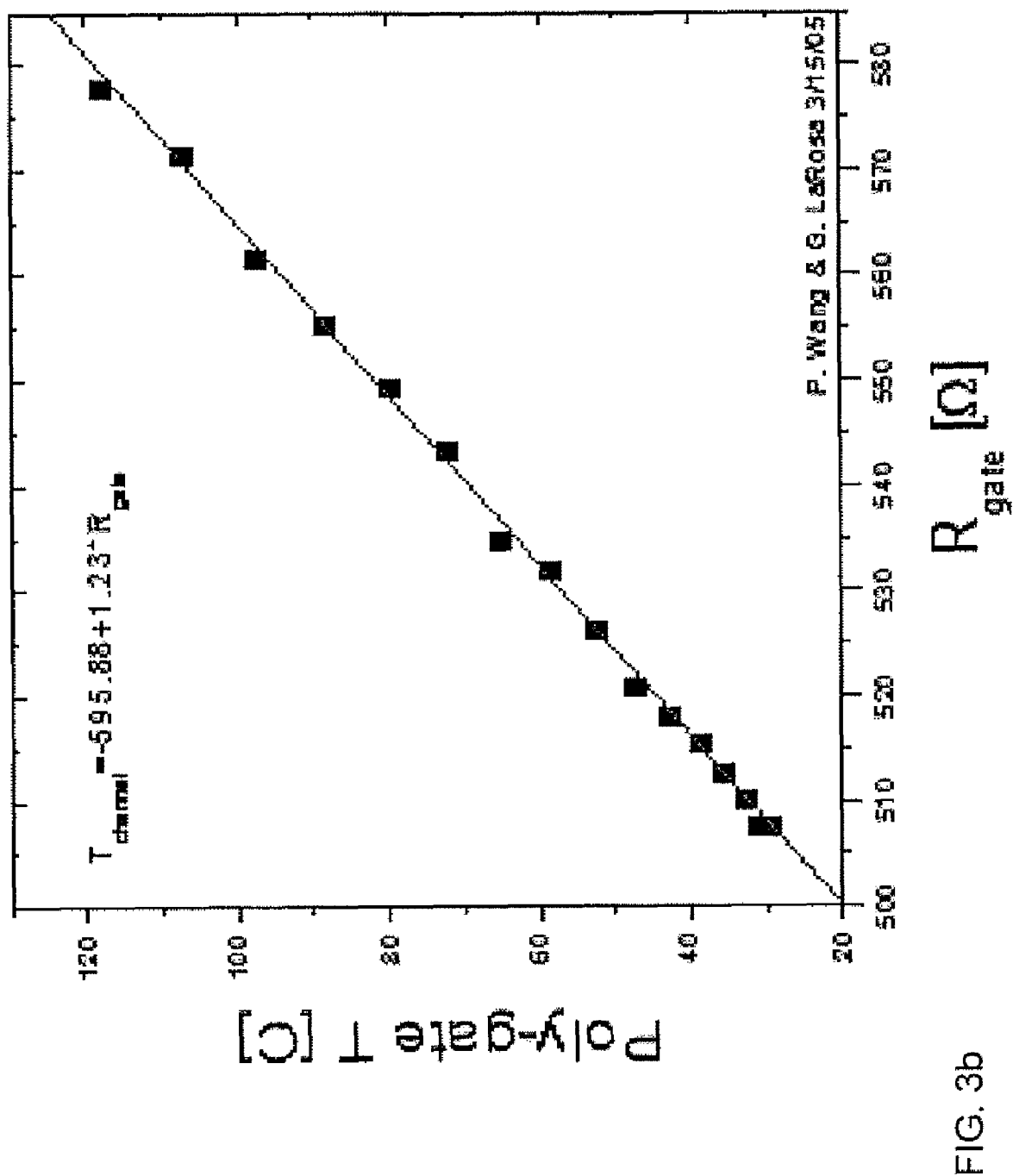
FIG. 3b is a graph showing gate resistance (in ohms) versus poly gate temperature.

FIG. 3b is a plot of the poly gate temperature versus gate resistance determined from the calibration of FIG. 3a. More particularly, the gate resistance of FIG. 3b is obtained in the previous calibration plot of FIG. 3a, e.g., the slope of the curve of FIG. 3a. Given the poly-gate resistances, it is possible to determine the corresponding temperatures using the correlations in FIG. 3b (since the temperature of each $V_{heater}$ is known). That is, since resistance is a function of temperature, it is possible to obtain a temperature for a known resistance using the calibration curve of FIG. 3a (and FIG. 3b).

Thus, based on the R-T (resistance-temperature) correlation of the poly gate in FIG. 3b, the poly gate temperature can be determined at a given device operating condition. In one example of FIG. 3b, the temperature at a gate resistance $R_{gate}$=540 ohms is approximately 70° C.

Figure 4A:
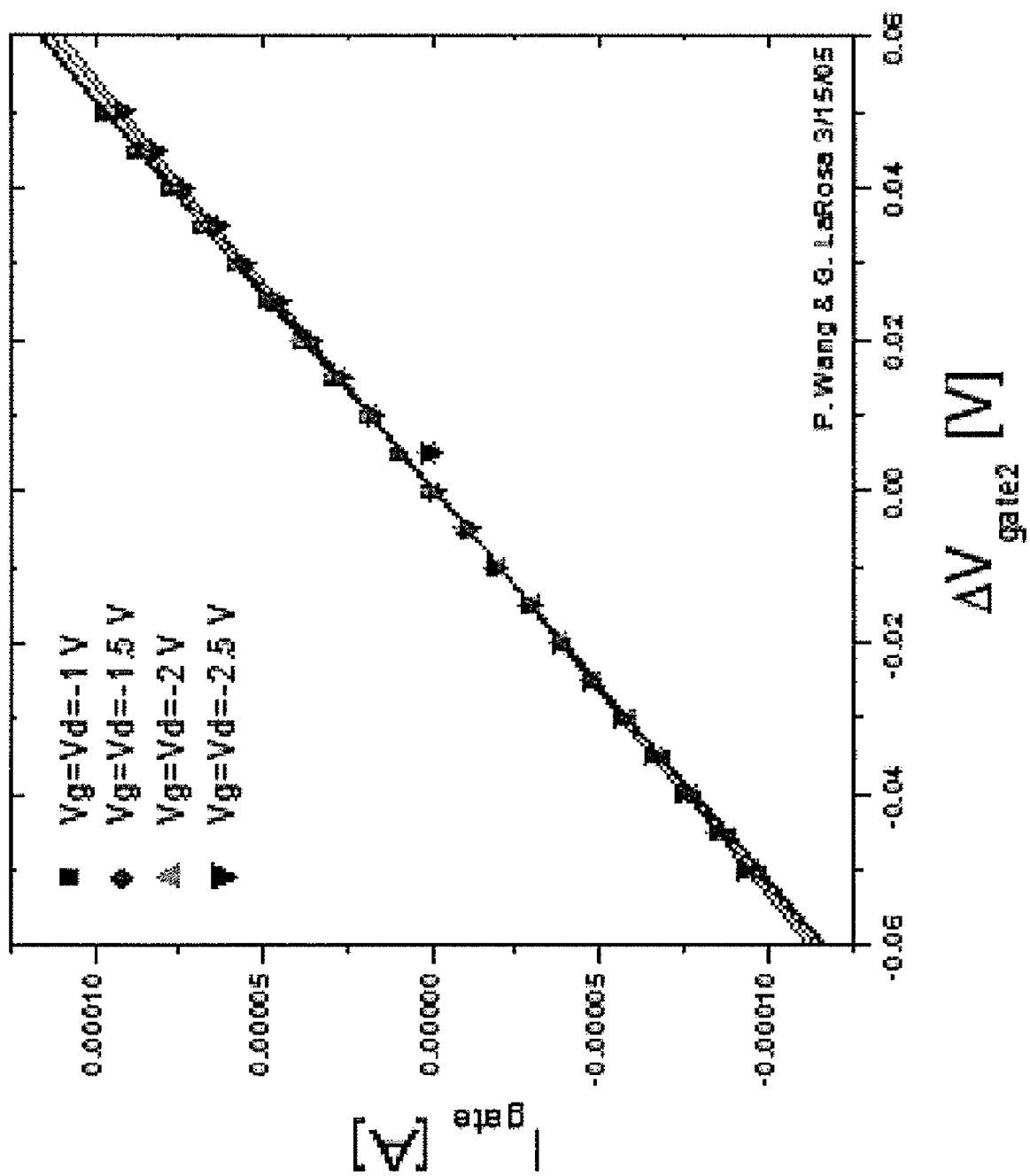
FIG. 4a is a graph showing gate voltage plotted against gate current.

FIG. 4a is a plot of voltage versus gate current for a given device which is powered up. To obtain this plot, currents $I_{drain}$ are flowing from the source to the drain at the respective operating conditions (e.g. $V_{gate}$=$V_{drain}$=-1V, -1.5V, etc. in this example), with a small voltage drop being applied across the gate (e.g. ±50 mV in this example). The voltages applied in this given scenario for determining self-heating under certain operating conditions are:

$V_{gate}$=$V_{drain}$=-1V;
$V_{gate}$=$V_{drain}$=-1.5V;
$V_{gate}$=$V_{drain}$=-2V; and
$V_{gate}$=$V_{drain}$=-2.5V.

It should be understood that the voltages shown herein are provided for illustrative purposes and should not be construed as a limiting feature to the invention. It should thus be understood that other voltage values can be implemented within the principles of the invention. The slope of the plot of FIG. 4a represents the resistance of the given device at a given operating bias condition.

Figure 4B:
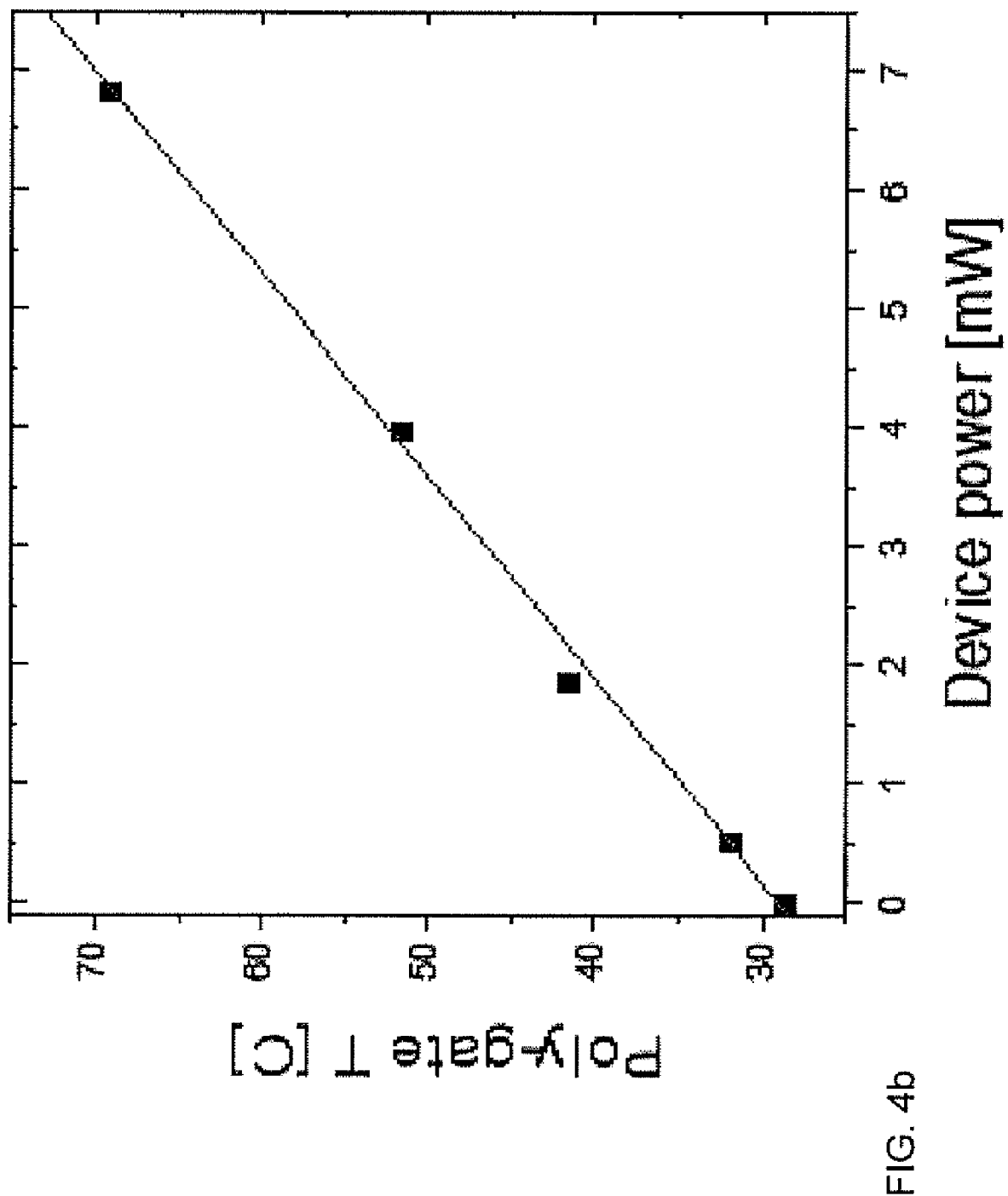
FIG. 4b is a graph showing device power versus poly gate temperature.

FIG. 4b shows a plot of the device power (mW) versus the poly gate temperature for the given device of FIG. 4a. As is well known, the device power is equivalent to the voltage multiplied by the current, or $V_{drain} \times I_{drain}$. As discussed above, using the plots of FIG. 3b and FIG. 4a, it is possible to obtain the temperature of the device at various power levels.

FIG. 5 shows a graph plotting the channel temperatures of the monitor devices 102. More specifically, the graph of FIG. 5 represents the projection of the channel temperature by plotting the temperature of the monitor devices 102 at different distances from the heating device 100.

As shown in FIG. 5, the channel temperature decays (decreases) as the monitor devices 102 move farther away from the heating device 100. Once temperatures are determined for certain distances of the monitor devices 102, a curve can be fitted to the temperature which is extrapolated to a zero distance from the heating device 100. The zero distance will represent the channel temperature of the heating device 100.

Thus, by performing an $I_{drain}/V_{gate}$ sweep of the monitor devices 102 (using sub-threshold slope) to measure the channel temperature of each monitor device 102 at various distances from the heating device 100, the temperature distribution in the $R_x$ area can be determined. And, as shown schematically in FIG. 5, the channel temperature of the heating device 100 can be determined by extrapolating the curve to zero distance from the heating device 100. (It should be recognized by those of skill in the art that an $I_{drain}/V_{gate}$ sweep cannot be performed on a powered up device as the device is biased at constant voltages during operation. As such, the $I_{drain}/V_{gate}$ sweep is not performed on the heating device.)

In embodiments, the $\Delta T$ is the difference in temperature between the poly-gate and channel across the gate oxide of the heating device 100. As mentioned previously, the $\Delta T$ is a thermal property of the gate oxide and, to the first order, does not depend (substantially independent) on the configuration and environment of the device involved. Therefore, the device channel temperature can be exactly determined from the $\Delta T$ value once the poly-gate resistance is measured, regardless of its configuration and environment.

Once the $\Delta T$ value is determined, it is possible to use this $\Delta T$ value to obtain the channel temperature of a device under different operating/stress conditions by only measuring the poly-gate resistance for different configurations and environments. By way of an illustrative example, knowing the ΔT value, it is possible to add this ΔT value to the gate temperature of a given device under operating/stress conditions to obtain the channel temperature of the given device.

Figure 6A:
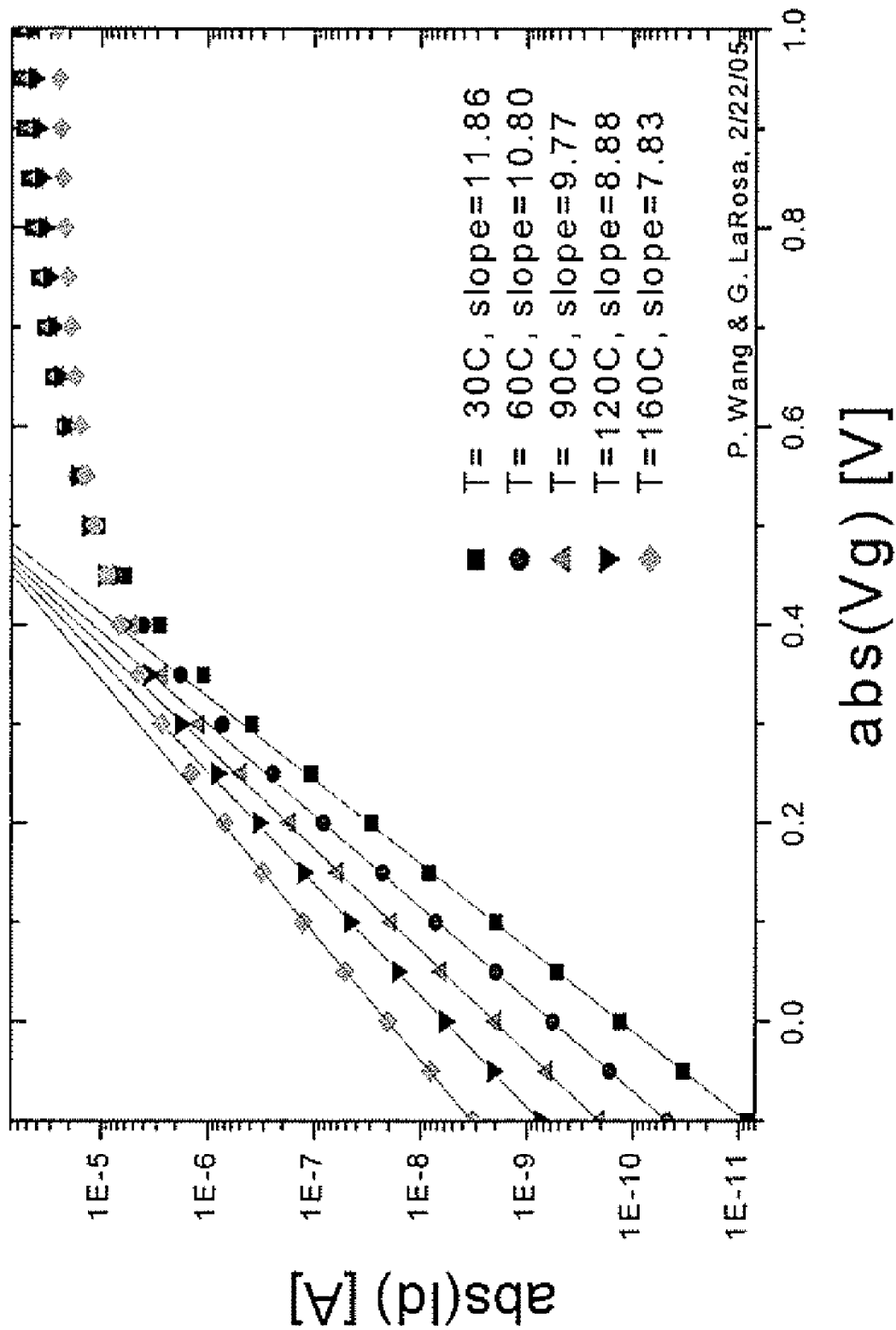
FIGS. 6a and 6b graphically show process steps of obtaining sub-threshold values for monitor devices.
Figure 6B:
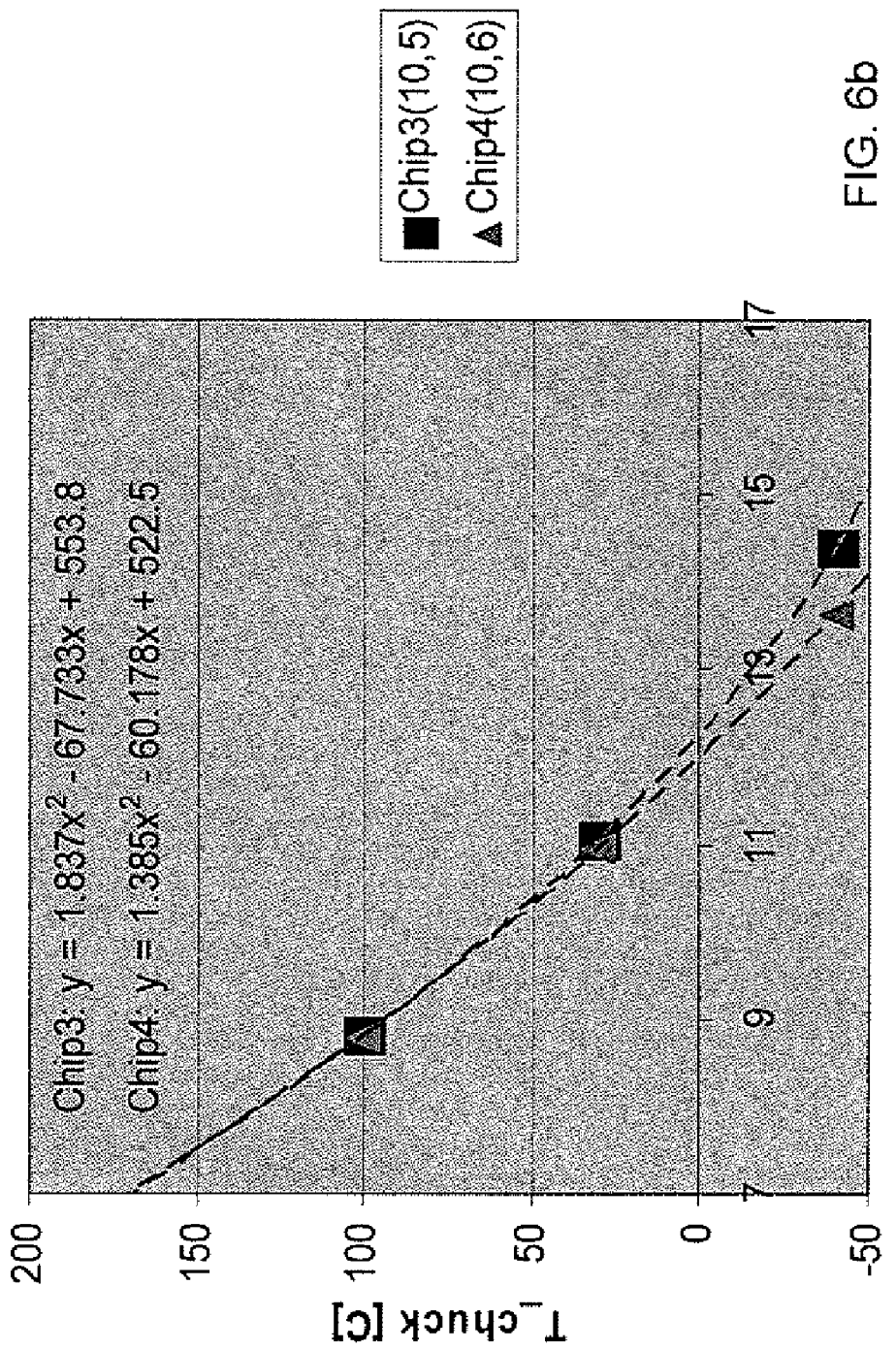

FIGS. 6a and 6b graphically show process steps of obtaining sub-threshold values for monitor devices. More specifically, FIG. 6a shows representative slopes of the $I_{drain}/V_{gate}$ sweep. In this illustrative non-limiting example, temperature is plotted over 30 degree intervals. The plotted points are fitted to a straight line which provides a slope and related values. The values of FIG. 6a are then used to obtain the plot of FIG. 6b, which is a graph of sub-threshold versus temperature. These values are one illustrative example, all of which values can be obtained by those of ordinary skill in the art.

Figure 7:
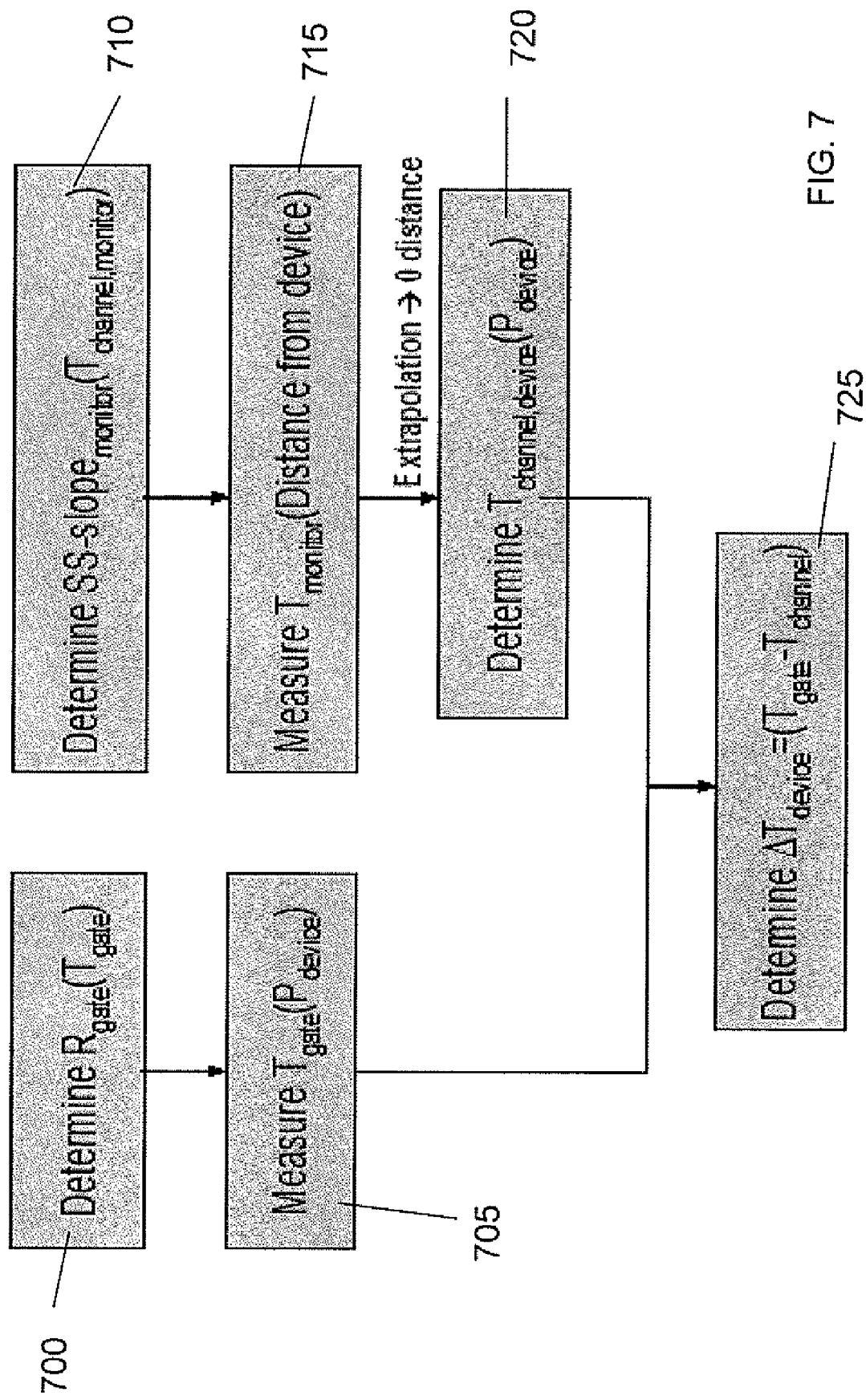
FIG. 7 is a flow chart showing processes in accordance with the invention.

FIG. 7 shows a flow diagram implementing process steps in accordance with the invention. The steps of FIG. 7 can be implemented in the infrastructure of FIG. 8. FIG. 7 may equally represent a high-level block diagram of the invention. The steps of FIG. 7 may be implemented and executed from either a server, in a client server relationship, or they may run on a user workstation with operative information conveyed to the user workstation to perform the calculations described above. Additionally, the invention can take the form of an entirely hardware embodiment, an entirely software embodiment or an embodiment containing both hardware and software elements. The software and/or computer program product can be implemented in the environment of FIG. 8, as should be understood and capable of implementation by those of skill in the art.

Referring still to FIG. 7, at step 700, the process determines the gate resistance for the heating device. As discussed above, the gate resistance is a function of the gate temperature, which is known for certain voltages. At step 705, the process determines the gate temperature of the heating device by plotting the power versus current. At step 710, the sub-threshold slope is determined for the monitor devices. At step 715, the temperatures of the monitor devices are measured at the various distances. At step 720, the channel temperature of the heating device is determined by extrapolating the temperatures of the monitor devices to zero distance from the heating device. At step 725, the ΔT value is obtained by subtracting the channel temperature from the gate temperature. As discussed above, the ΔT value can then be used to determine the channel temperature for different devices under different operating conditions/stresses.

Figure 8:
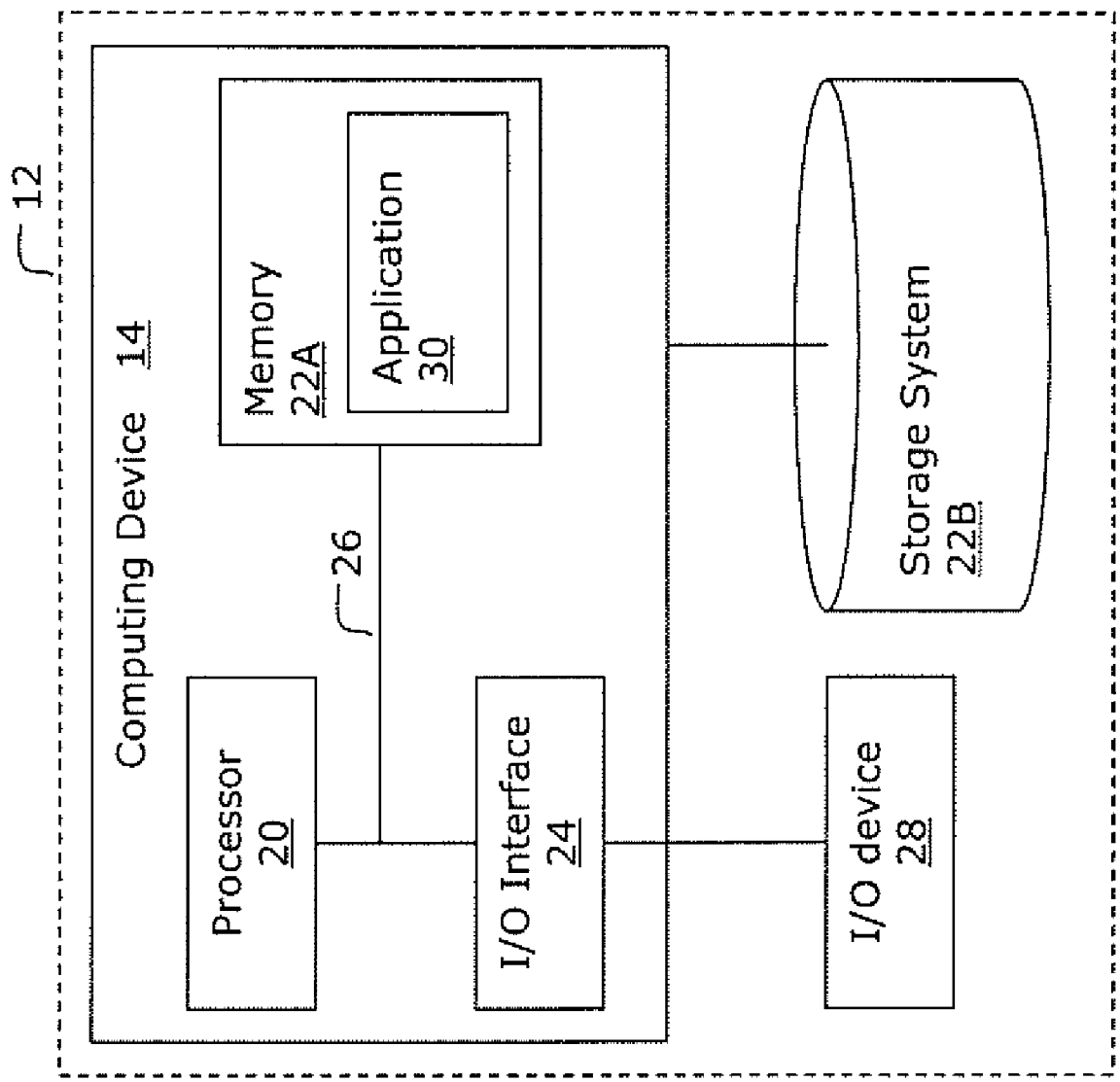
FIG. 8 shows an illustrative environment which implements the processes of FIG. 7.

FIG. 8 shows an illustrative environment 10 for managing the processes in accordance with the invention. To this extent, the environment 10 includes a computer infrastructure 12 that can perform the processes described herein. In particular, the computer infrastructure 12 includes a computing device 14 that comprises a management system 30, which makes computing device 14 operable to perform the process described herein. The computing device 14 includes a processor 20, a memory 22A, an input/output (I/O) interface 24, and a bus 26. Further, the computing device 14 is in communication with an external I/O device/resource 28 and a storage system 22B.

As is known in the art, in general, the processor 20 executes computer program code, which is stored in memory 22A and/or storage system 22B. While executing computer program code, the processor 20 can read and/or write data to/from memory 22A, storage system 22B, and/or I/O interface 24. The bus 26 provides a communications link between each of the components in the computing device 14. The I/O device 28 can comprise any device that enables an individual to interact with the computing device 14 or any device that enables the computing device 14 to communicate with one or more other computing devices using any type of communications link.

The computing device 14 can comprise any general purpose computing article of manufacture capable of executing computer program code installed thereon (e.g., a personal computer, server, handheld device, etc.). However, it is understood that the computing device 14 is only representative of various possible equivalent computing devices that may perform the processes described herein. To this extent, in embodiments, the functionality provided by computing device 14 can be implemented by a computing article of manufacture that includes any combination of general and/or specific purpose hardware and/or computer program code. In each embodiment, the program code and hardware can be created using standard programming and engineering techniques, respectively.

Similarly, the computer infrastructure 12 is only illustrative of various types of computer infrastructures for implementing the invention. For example, in embodiments, the computer infrastructure 12 comprises two or more computing devices (e.g., a server cluster) that communicate over any type of communications link, such as a network, a shared memory, or the like, to perform the process described herein. Further, while performing the process described herein, one or more computing devices in the computer infrastructure 12 can communicate with one or more other computing devices external to computer infrastructure 12 using any type of communications link. The communications link can comprise any combination of wired and/or wireless links; any combination of one or more types of networks (e.g., the Internet, a wide area network, a local area network, a virtual private network, etc.); and/or utilize any combination of transmission techniques and protocols.

In embodiments, the invention provides a business method that performs the process steps of the invention on a subscription, advertising, and/or fee basis. That is, a service provider, such as a Solution Integrator, could offer to perform the processes described herein. In this case, the service provider can create, maintain, support, etc., a computer infrastructure that performs the process steps of the invention for one or more customers. In return, the service provider can receive payment from the customer(s) under a subscription and/or fee agreement and/or the service provider can receive payment from the sale of advertising content to one or more third parties.

The method as described above is used in the fabrication of integrated circuit chips. The resulting integrated circuit chips can be distributed by the fabricator in raw wafer form (that is, as a single wafer that has multiple unpackaged chips), as a bare die, or in a packaged form. In the latter case the chip is mounted in a single chip package (such as a plastic carrier, with leads that are affixed to a motherboard or other higher level carrier) or in a multichip package (such as a ceramic carrier that has either or both surface interconnections or buried interconnections). In any case the chip is then integrated with other chips, discrete circuit elements, and/or other signal processing devices as part of either (a) an intermediate product, such as a motherboard, or (b) an end product. The end product can be any product that includes integrated circuit chips, ranging from toys and other low-end applications to advanced computer products having a display, a keyboard or other input device, and a central processor.

While the invention has been described in terms of exemplary embodiments, those skilled in the art will recognize that the invention can be practiced with modifications and in the spirit and scope of the appended claims.

It is claimed:

1. A method, comprising:
   determining a poly-gate temperature for a given device;
   determining channel temperatures of monitor devices;
   extrapolating channel temperatures of the monitor devices to obtain a channel temperature for the given device; and
   determining a temperature difference, ΔT value, for the given device based on the poly-gate temperature and the channel temperature.

2. The method of claim 1, wherein the channel temperatures are determined using sub-threshold slopes.

3. The method of claim 2, wherein the sub-threshold slopes are determined by an $I_{drain}/V_{gate}$ sweep.

4. The method of claim 1, wherein the extrapolating comprising bringing a distance measurement to a zero distance from the given device.

5. The method of claim 1, wherein the ΔT value is obtained for the given device at a given gate oxide thickness.

6. The method of claim 1, wherein the ΔT value is a thermal property of the gate oxide which is substantially independent of geometry and environment.

7. The method of claim 1, wherein the given device is a heating device which is not powered up during the determining of the poly gate temperature.

8. The method of claim 1, wherein the poly-gate temperature is determined by measuring a resistance across the poly gate.

9. The method of claim 1, further comprising determining a channel temperature for a second device by subtracting the gate poly temperature of the second device from the ΔT value.

10. The method of claim 1, further comprising providing at least one contact at each end of the poly gate of the given device.

11. The method of claim 1, wherein the poly gate temperature is determined by plotting voltage versus gate current for a heating device over a range of voltages at known temperatures to obtain a resistance and plotting the resistance against temperature to determine the poly gate temperature.

12. A method comprising:
    measuring a poly-gate temperature for a heating device which is not powered up;
    determining channel temperatures of monitor devices by use of sub-threshold slopes;
    extrapolating channel temperatures of the monitor devices to a zero distance to the heating device in order to obtain a channel temperature of the heating device; and
    determining a temperature difference, ΔT value, for the heating device between the channel temperature and the poly-gate temperature.

13. The method of claim 12, wherein the sub-threshold slopes are determined by an $I_{drain}/V_{gate}$ sweep.

14. The method of claim 12, wherein the ΔT value is obtained for the heating device at a given gate oxide thickness.

15. The method of claim 12, wherein the poly-gate temperature is determined by measuring a resistance across the poly gate.

16. The method of claim 12, further comprising determining a channel temperature for a second device by subtracting the gate poly temperature of the second device from the ΔT value.

17. The method of claim 12, wherein the poly gate temperature is determined by plotting voltage versus gate current for the heating device over a range of voltages at known temperatures to obtain a resistance and plotting the resistance against temperature to determine the poly gate temperature.

18. The method of claim 12, wherein the heating device includes at least one contact at each end of the gate.

\* \* \* \* \*